(12) United States Patent
Chen et al.

(10) Patent No.: US 10,155,081 B2
(45) Date of Patent: Dec. 18, 2018

(54) TELE-CARE MANAGEMENT SYSTEMS AND METHODS FOR PERITONEAL DIALYSIS

(71) Applicants: NATIONAL TSING HUA UNIVERSITY, Hsinchu (TW); NATIONAL TAIWAN UNIVERSITY, Taipei (TW); NATIONAL TAIWAN UNIVERSITY HOSPITAL, Taipei (TW)

(72) Inventors: Hung-Shao Chen, Hsinchu (TW); Jenq-Wen Huang, Hsinchu (TW); Hsi-Pin Ma, Hsinchu (TW)

(73) Assignees: NATIONAL TSING HUA UNIVERSITY, Hsinchu (TW); NATIONAL TAIWAN UNIVERSITY, Taipei (TW); NATIONAL TAIWAN UNIVERSITY HOSPITAL, Taipei (TW)

( * ) Notice: Subject to any disclaimer, the term of this patent is extended or adjusted under 35 U.S.C. 154(b) by 239 days.

(21) Appl. No.: 15/132,117

(22) Filed: Apr. 18, 2016

(65) Prior Publication Data

US 2017/0136166 A1    May 18, 2017

(30) Foreign Application Priority Data

Nov. 13, 2015   (TW) .............................. 104137464 A

(51) Int. Cl.
| | |
|---|---|
| *G01N 33/48* | (2006.01) |
| *G01N 33/50* | (2006.01) |
| *A61M 1/28* | (2006.01) |
| *G01F 23/296* | (2006.01) |
| *G01N 21/25* | (2006.01) |
| *G06F 19/00* | (2018.01) |
| *G01N 21/51* | (2006.01) |
| *A61M 1/16* | (2006.01) |

(52) U.S. Cl.
CPC .......... *A61M 1/282* (2014.02); *A61M 1/1609* (2014.02); *A61M 1/28* (2013.01); *G01F 23/2962* (2013.01); *G01N 21/251* (2013.01); *G01N 21/255* (2013.01); *G01N 21/51* (2013.01); *G06F 19/3418* (2013.01); *A61M 2205/331* (2013.01); *A61M 2205/3375* (2013.01); *A61M 2205/3553* (2013.01); *A61M 2205/3592* (2013.01); *A61M 2205/502* (2013.01); *G01N 2201/062* (2013.01); *G01N 2201/12* (2013.01)

(58) Field of Classification Search
None
See application file for complete search history.

(56) References Cited

U.S. PATENT DOCUMENTS

| | | | | |
|---|---|---|---|---|
| 5,643,201 | A * | 7/1997 | Peabody | A61M 1/1686 604/29 |
| 7,663,751 | B1 * | 2/2010 | Mitchell | G01N 21/51 356/339 |
| 2006/0167531 | A1 * | 7/2006 | Gertner | A61N 5/0603 607/86 |
| 2008/0045884 | A1 | 2/2008 | Landherr et al. | |
| 2010/0005416 | A1 | 1/2010 | Hedmann et al. | |
| 2013/0303865 | A1 * | 11/2013 | Rebec | A61B 5/0082 600/310 |
| 2014/0242612 | A1 * | 8/2014 | Wang | G01N 21/253 435/7.23 |

FOREIGN PATENT DOCUMENTS

| | | |
|---|---|---|
| CN | 104225699 | 12/2014 |
| CN | 204016965 | 12/2014 |
| TW | 201328738 | 7/2013 |
| TW | M492163 | 12/2014 |

* cited by examiner

*Primary Examiner* — Russell S Negin

(57) ABSTRACT

A tele-care management system for peritoneal dialysis (PD) includes at least a container, a holder, a removable detection device and a mobile device. The container is for placing effluent fluid of peritoneal dialysis. The holder is for placing the container. The removable detection device includes a detection unit, a processor and a communication interface, wherein the processor detects the turbidity and the chrominance of the effluent fluid and performs a quantitative analysis on the effluent fluid, and generates a turbidity prediction value based on the detection result of the detection unit. The processor respectively calculates first and second turbidity values, which correspond to first and second turbidity respectively, for the effluent fluid according to first and second algorithms and selects one from the first and second turbidity values to generate the turbidity prediction value based on a predetermined threshold value sent to a mobile device for further processing.

12 Claims, 4 Drawing Sheets

TELE-CARE MANAGEMENT SYSTEMS AND METHODS FOR PERITONEAL DIALYSIS

CROSS REFERENCE TO RELATED APPLICATIONS

This application claims the benefit of Taiwan Patent Application No. 104137464, filed Nov. 13, 2015, the entirety of which is incorporated by reference herein.

BACKGROUND OF THE INVENTION

Field of the Invention

The disclosure relates generally to peritoneal dialysis (PD) and, more particularly to tele-care management systems for PD and related methods for PD thereof capable of providing easy self-management.

Description of the Related Art

Chronic renal failure patients must receive some form of long-term dialysis treatment. In particular, peritoneal dialysis is a form of dialysis that can be performed at home. Compared to patients that must pay regular hospital visits for hemodialysis, peritoneal dialysis features low costs and high efficiency, thus setting the trend of future promotion. Peritoneal dialysis (abbreviated as PD) is the implantation of a permanent catheter in the abdominal cavity. Through the catheter, the effluent fluid is poured into the abdominal cavity for a period of time. With the peritoneum as the semipermeable membrane for dialysis, wastes that cannot be metabolized by the kidneys and excessive water are moved to the effluent fluid in the abdominal cavity to be excreted outside the body and for new effluent fluid to be introduced. This gives patients the option of performing peritoneal dialysis at home and for them to supply their recycled effluent fluid for a doctor in the hospital to determine its turbidity through the naked eye and decide subsequent therapy to be administered.

However, occurrences of peritonitis and other complications tend to hamper the PD implementation. The effluent fluid for PD often shows variations, depending on the physical condition of the patient. In other words, the effluent fluid for PD can be used to determine whether or not certain lesions occur in peritoneal dialysis users. However, when such lesions become detectable by the naked eye, it is often too late. Meanwhile, since the patient may only be able to pay a revisit to the doctor every month or after longer time, the doctor may not be able to monitor the patient's condition between two visits and provide the patient with early treatment where appropriate.

BRIEF SUMMARY OF THE INVENTION

Tele-care management systems for peritoneal dialysis (PD) and related methods for PD thereof are provided.

An embodiment of the invention provides a tele-care management system for peritoneal dialysis (PD) includes at least a container, a holder, a removable detection device and a mobile device. The container is for placing effluent fluid of peritoneal dialysis. The holder is for placing the container. The removable detection device includes a detection unit, a processor and a communication interface, wherein the processor detects the turbidity and the chrominance of the effluent fluid and performs a quantitative analysis on the effluent fluid, and generates a turbidity prediction value based on the detection result of the detection unit. The processor respectively calculates first and second turbidity values, which correspond to first and second turbidity respectively, for the effluent fluid according to first and second algorithms and selects one from the first and second turbidity values to generate the turbidity prediction value based on a predetermined threshold value sent to a mobile device for further processing.

Another embodiment of the invention provides a method for peritoneal dialysis (PD) applied to a tele-care management system for PD, the method comprising the steps of: receiving an analysis request; in response to the analysis request, using a removable detection device to perform a quantitative analysis on an effluent fluid of PD and respectively calculate a first turbidity value which corresponds to a first turbidity for the effluent fluid according to a first algorithm and a second turbidity value which corresponds to a second turbidity for the effluent fluid according to a second algorithm; selecting one from the first and second turbidity values to generate a turbidity prediction value based on a predetermined threshold value; and transmitting the turbidity prediction value to a mobile device application for display.

Methods for peritoneal dialysis (PD) may take the form of a program code embodied in a tangible media. When the program code is loaded into and executed by a machine, the machine becomes an apparatus for practicing the disclosed method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. It should be understood that the embodiments may be realized in software, hardware, firmware, or any combination thereof.

Embodiments of the invention provide tele-care management systems and method for peritoneal dialysis (hereinafter referred as PD), which involve the use of a portable/removable detection device, coupled with some detection units and microprocessors. Additionally, a mobile device application (APP) at the mobile device end for peritoneal dialysis home care has been developed to assist patients through hands-on operations and provide real-time detection, thereby facilitating home management by PD users and establishing the first line of defense for PD, while ensuring the early detection of peritonitis and other complications at their onset and enabling relevant medical units to perform real-time disposal and proper adjustment to the therapy.

Figure 1:
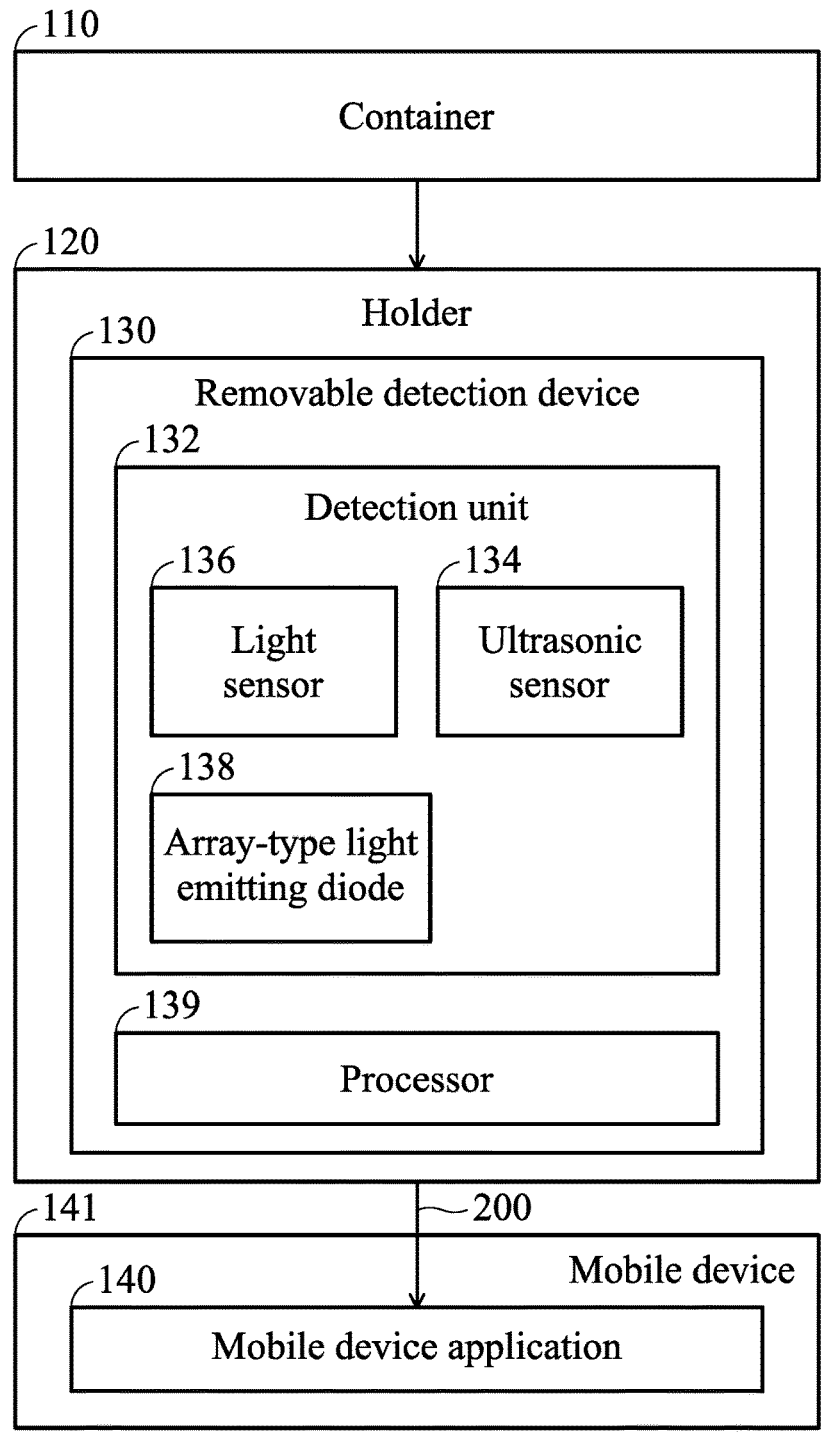
FIG. 1 is a schematic diagram illustrating an embodiment of a tele-care management system for PD of the invention.

FIG. 1 is a schematic diagram illustrating an embodiment of a tele-care management system 100 for PD of the invention. The tele-care management system 100 for PD at least includes a container 110 for placing effluent fluid for PD, a holder 120, a removable detection device and a mobile device application 140 at the mobile device end operated by the PD user, which is installed on mobile device 141.

The container 100 for placing effluent fluid for PD is a special container whose size can accommodate most of the effluent fluid discharged by the PD user (hereinafter referred to as the patient). For example (but not limited to), the container 110 may be a rectangular container made of translucent acrylic material; it may measure 9*9*30 cm in size and 2430 ml in volume.

The holder 120 may have a portable design, which is used to place the container 110. The detection device 130 may include at least one detection unit 132, which includes several sensors and components, such as an ultrasonic sensor 134, a light sensor 136 and an array-type light emitting diodes 138, which are used to quantify the effluent fluid and detect the turbidity/concentration. The ultrasonic sensor 134 and the light sensor 136 are fixated on the holder 120 and are controlled by the processor 139. The processor 139 may be a Central Processing Unit (CPU), Micro-Control Unit (MCU), Digital Signal Processor (DSP), or the like, which provides the function of data processing and computing. More particularly, the processor 139 may load and execute a series of instructions and/or program codes to control the operation of the detection unit 132 in the detection device 130 for performing the method for PD of the invention.

Figure 2:
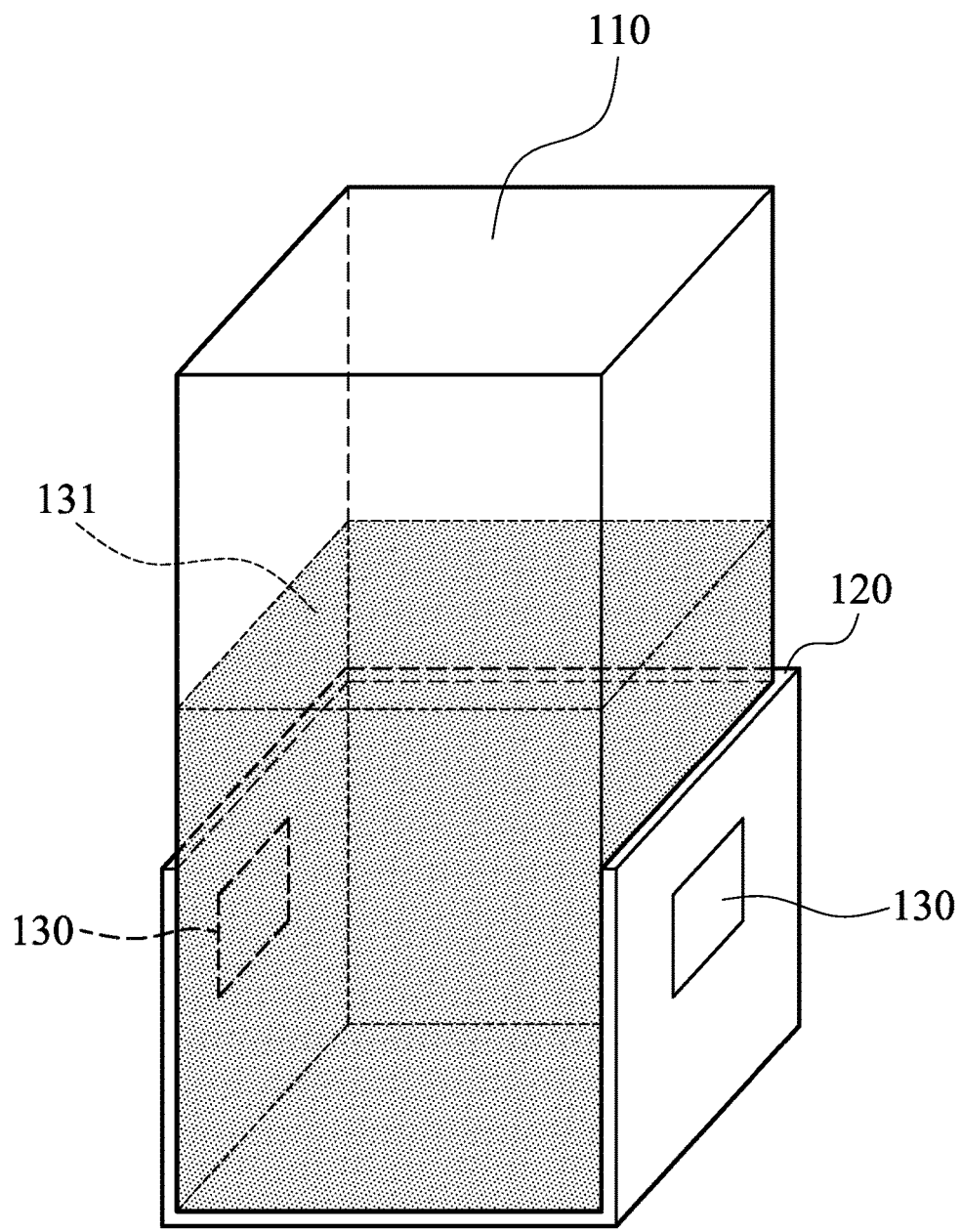
FIG. 2 is a schematic diagram illustrating an embodiment of architecture of the tele-care management system for PD of the invention.

FIG. 2 is a schematic diagram illustrating an embodiment of architecture of the tele-care management system 100 for PD of the invention. As shown in FIG. 2, the container 110 contains effluent fluid 131 poured in by the patient. Moreover, the holder 120 has a portable design and a fixed surface area. It may also have an acrylic base design for placing the container 110. In the detection device 130, the ultrasonic sensor 134, the light sensor 136 and the array-type light emitting diodes 138 are fixed on corresponding locations on the holder 120. Particularly, the detection unit 132 in the detection device 130 (such as: the light sensor 136 and the array-type light emitting diodes 138) are placed on the left and right sides of the holder 120, rather than on the container 110. For example, the detection unit 132 is placed in corresponding locations of both sides with the same height, and their locations are subject to adjustment.

After the patient collects the PD exchange fluid in the collecting bag, it can be drained into the container 110. Then, the container 110 is placed on the holder 120 for detection. After the measurement is completed, the effluent fluid is discarded and the container is washed to complete one measurement. In the embodiments, after the patient performs PD, the effluent fluid can be directly poured into the container 110 to measure the height through the ultrasonic sensor, without polluting the sensor and container. Thus, the container and holder can be reused.

The ultrasonic sensor 134 may detect the time difference between ultrasound transmission and reception in an acoustic manner and then convert it into the height of the effluent fluid to obtain the volume. Additionally, by comparing the quantitative objective and one's average discharge, whether or not a certain lesion is about to occur can be determined. In an acoustic manner, the ultrasonic sensor 134 can detect the time difference between ultrasonic wave transmission and reception, based on which the volume of effluent fluid recycled can be converted. For example, the following equation can be used for converting the volume of the recycled effluent fluid (abbreviated as effluent fluid):

$$\text{Distance}=\text{Time}/58, \text{volume}=\text{distance}*81 \qquad (1),$$

wherein in formula (1), the time is defined as the time interval of each pulse, where 58 is the time spent by the sound velocity per 1 cm run, and 81 is a fixed size of the surface area of the container. It should be understood that the quantitative objective and one's average discharge volume are compared in order to determine if a certain lesion is about to occur. The discharge volume represents the volume of the effluent fluid detected, while the average discharge volume represents the average volume of the effluent fluid detected for a number of times for the patient. According to the clinical diagnosis, the difference between the volume of the effluent fluid detected in a specific measurement and the average discharge reaches over 2000 ml may mean certain lesions are about to occur. For example, assuming the patient's average discharge volume is 250 ml, then, the discharge volume of one-time effluent fluid is 500 ml. Since the difference between the two reaches 200 ml, it can be determined that certain lesions are about to occur. Therefore, an immediate re-visit can be arranged for further examination and therapy adjustment, if needed.

Each transmission and reception of the light sensor 136 and the array-type light emitting diodes 138 can be used to determine the PD effluent fluid turbidity/concentration indicators. In some embodiments, the light sensor 136 and the light-emitting diode array 138 are placed on both sides of the holder 120, wherein the array-type light emitting diodes 138 can be used to provide light to the container 110, while the light sensor 136 can receive light that penetrates the container 110.

In one embodiment, the array-type light emitting diodes 138 can emit white light (with the electromagnetic wave of about 390~780 nm) and the light sensor 136 on the other end receives all visible wavelengths. Under this measurement mechanism, the greater the suspension in the effluent fluid, the lesser the light. This way, the turbidity and concentration of the effluent fluid can be determined. In some embodiments, the light sensor 136 may be a light-sensitive chip that transmits or receives light of a specific wavelength (such as: white light) and it can estimate the volume of the effluent fluid through ultrasonic detection.

The processor 139 may simultaneously calculate two turbidity values using two different turbidity algorithms and then determine which between the two is the turbidity estimation value based on one determination criterion (such as: the match of one threshold value). To be more specific, the processor 139 may calculate a first turbidity value of a first turbidity for the effluent fluid in the container 110 using the first algorithm and a second turbidity value of a second turbidity for the effluent fluid in the container 110 using the second algorithm. Additionally, based on the predetermined threshold value, either the first turbidity value or the second turbidity value is selected to generate the turbidity estimation value. For example, the first algorithm can be used to perform turbidity calculation on the effluent fluid that is clearer. The second algorithm can be used to perform turbidity calculation on the effluent fluid that is more turbid. For example, the first algorithm can be the beer's law algorithm and the second algorithm can be scattering or Rayleigh/Mie scattering. The threshold value can be determined based on experience and expert recommendations (e.g. the value provided by the clinician based on his or her years of experience) to determine which between the two is the turbidity estimation value.

For example, in one embodiment, the first turbidity value is selected when the calculated turbidity value conforms to certain conditions or the second turbidity value is selected when the turbidity value calculated does not conform to certain conditions. In some embodiments, the above conditions can be self-defined by the user, or they can be obtained based on user experience. For example, when the second turbidity value (scattering or Rayleigh/Mie scattering) fails to identify significant differences (the value tested >120 lux), it means the liquid is without obvious suspension and is more homogeneous. Therefore, it is switched to the first turbidity value to calculate the concentration of the substance in the liquid. The first turbidity value is calculated using the Beer's law.

By Beer's law defined as follows:

$$A=\varepsilon lc,$$

where A represents absorbance, c represents the absorption coefficient, l represents the optical path length and c represents the concentration of the liquid.

Changing the emission wavelength of incidence light and the corresponding frequency response received by the sensor can determine the concentration of certain chemical substances (protein, creatinine) under lower turbidity and with more homogenous effluent fluid in the peritoneum. Clinically, the degree of peritonitis onset has as positive correlation with the chemical substances. Hence, they can be regarded as determination indicators.

The detection device 130 may further provide a communication interface 200 for communications with the mobile device client application 140 on the mobile device 141 therethrough. The communication interface 200 may support various communications protocols, such as the code division multiple access (CDMA), Global System for Mobile Communications (GSM), Enhanced Data GSM Environment (EDGE), High-Speed Downlink Packet Access (HSDPA), Wi-Fi (such as IEEE 802.11a/b/g/n), Bluetooth, and Wi-MAX communication protocol, and other protocols, but the invention is not limited thereto. It should be understood that the detection device 130 and the mobile device 141 (e.g., the smart phone) may respectively include communication modules supporting communication protocol being used to establish the desired wireless connection.

As above-mentioned, the mobile device client application 140 is installed on the mobile device. For example, the mobile device 140 can be any types of portable device or handheld device, such as a PDA, a smartphone, a mobile phone, a tablet, an MID, a laptop computer, a car computer, a digital camera, a multimedia player or a game device, or any other type of mobile computational device, however, it is to be understood that the invention is not limited thereto. The mobile device client application 140 refers to any application installed on any of the aforementioned portable devices or handheld devices.

The mobile device client application 140 may further provide a graphical user interface (e.g., one phone GUI interface for operating by patients), which is used to obtain effluent turbidity and chrominance values detected or measured by the detection device 130 through the communication interface 200. Then, the values can be stored or uploaded in one cloud medical system or a specific third party (such as: the mobile phone of the attending physician) for further processing. For example, the mobile device application 140 can upload, automatically or based on the user's setting, the analysis results to the cloud medical system in order to carry out subsequent remote monitoring or medical applications, such as the medical personnel can timely monitor the patient's condition, discover the patient's physiological status changes, and take the initiative to notify the patient to make an early revisit for timely treatment based on the peritoneal dialysis analysis results uploaded from a remote end.

Figure 3:
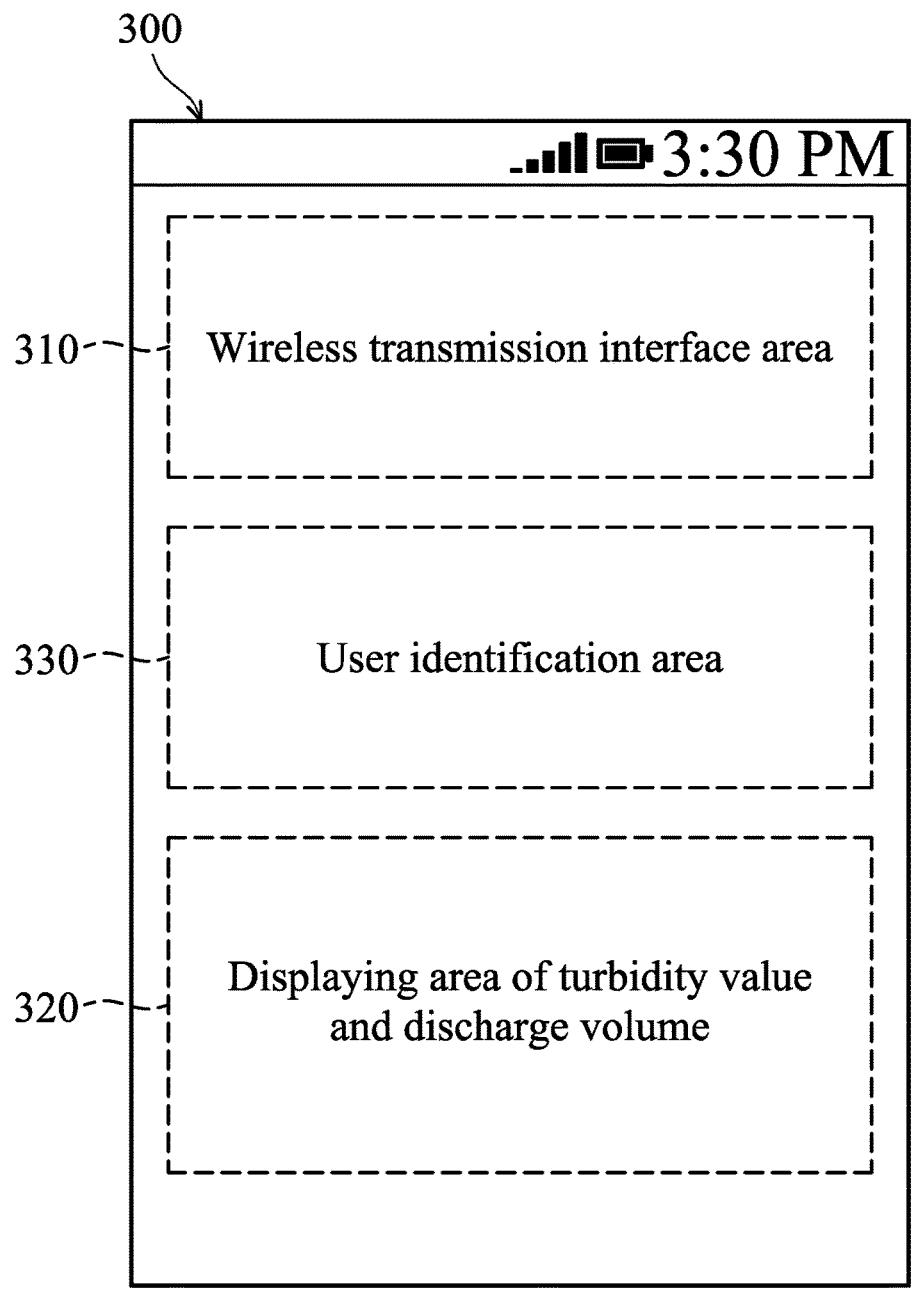
FIG. 3 is a schematic diagram illustrating an embodiment of a graphical user interface (UI) of a mobile device application of the invention.

FIG. 3 is a schematic diagram illustrating an embodiment of a graphical user interface (UI) 300 of the mobile device application of the invention. As shown in FIG. 3, the graphical UI 300 of the mobile device application may include several areas, from 310-330. Among them, area 310 is also known as the wireless transmission interface area which is provided for the user to request for connecting with the detection device 130, and is also used to indicate the connection status (e.g., Whether or not Bluetooth connection is successful). The area 320 is also known as the user identification area, which is used to determine and distinguish different users. After the patient completes peritoneal dialysis and pours the effluent fluid into the container 110 for analysis, the mobile device application 140 can be activated. In one embodiment, after the mobile device application 140 is activated, the UI 300 is displayed. The patient may enter the patient number in the area 320 and press the button on the area 310 to request to connect with the detection device through the Bluetooth. When successfully connected to the detection device 130, the processor 139 controls the detection unit 132 such as the light sensor 136, the ultrasonic sensor 34 and others to perform analysis on the abovementioned turbidity, chrominance, and volume. In addition, the analysis data will be sent to the mobile device 141 through the communication interface 200, such as the Bluetooth interface. After receiving the information from the processor 139, the mobile device application 140 on the mobile device 141 may display the analysis data received such as turbidity value, ultrasonic wave distance, and so on at the location of the area 330 (also known as displaying area of turbidity and discharge volume), thereby informing patients of the analysis results. Subsequently, the analysis information can be outputted into files to be directly stored and/or uploaded in the medical cloud through a wireless network such as WiFi or a mobile network. The information can be archived for patients to facilitate tracking and monitor by medical personnel.

Figure 4:
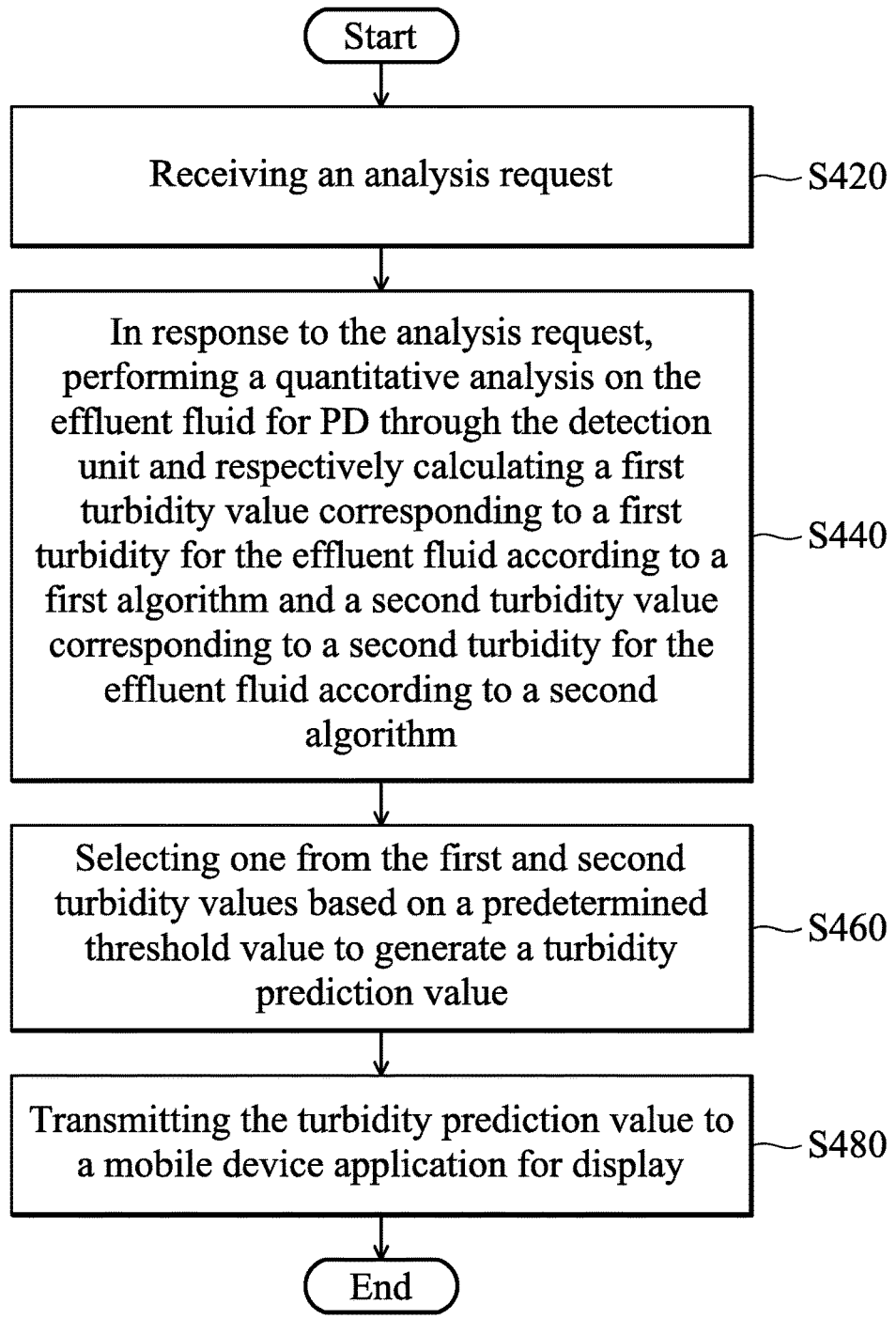
FIG. 4 is a flowchart of another embodiment of a method for PD of the invention.

Another embodiment of the present invention also provides a method for PD analysis. FIG. 4 is a flowchart of another embodiment of a method for PD of the invention. The method for PD analysis can be applied to a tele-care management system for PD, such as the tele-care management system 100 as shown in FIG. 1 and can be performed by the processor 139 of the tele-care management system 100.

First, the processor 139 receives an analysis request from a patient (step S402). For example, referring together to FIG. 3, the patient can press the button of the are 310 on the user interface 300 to issue the analysis request to request to connect to the detection device 130 in a Bluetooth connection and to perform analysis. Then, in response to the analysis request, the processor 139 performs a quantitative analysis on the effluent fluid for PD in the container 110 through the detection unit 132 of the detection device 130 and respectively calculates a first turbidity value corresponding to a first turbidity for the effluent fluid according to a first algorithm and a second turbidity value corresponding to a second turbidity for the effluent fluid according to a second algorithm (step S404). For example, the first algorithm can be used to calculate the turbidity of clearer effluent fluid (the first turbidity) while the second algorithm can be used to calculate the turbidity of more turbid effluent fluid (the second turbidity). For example, the first algorithm may be the Beer's law algorithm, and the second algorithm may be the scattering or Rayleigh/Mie scattering.

Subsequently, the processor 139 selects one from the first turbidity value and the second turbidity value based on a predetermined threshold value to generate the turbidity prediction value (step S406). The threshold value can be based on experience and expert recommendations (For example: the value provided based on the clinician's years of experience), thereby determining which of the two will be selected as the turbidity prediction value. For example, when the second turbidity value (calculated by scattering or Rayleigh/Mie scattering) fails to identify significant differences (the value measured >120 lux), it means the liquid is without obvious suspension and is more homogeneous. Therefore, it is switched to the first turbidity value to calculate the concentration of the substance in the liquid. The first turbidity value is calculated using Beer's law.

After the turbidity prediction value is generated, the processor 139 may further wirelessly transmit the turbidity prediction value to a mobile device application (e.g., the mobile device application 140) for display via a communication interface, such as a Bluetooth interface (step S408). Therefore, the analysis results can be displayed through the user interface 300 on the mobile device client application 140 as shown in FIG. 3. Through this user interface 300, the patient can conveniently engage in home care and self-management.

In some embodiments, the mobile device application 140 may further capture an image of the effluent fluid through an image capture device (e.g., a CCD lens module or camera) and perform an image processing procedure on the effluent fluid image captured in order to analyze the turbidity and chrominance of the effluent fluid. The abovementioned image processing procedure may include the steps of capturing an image including the effluent fluid and performing a color calibration and compensation operation on the captured image so as to analyze the turbidity and chrominance of the effluent fluid.

For example, in one embodiment, color calibration and compensation operation may further be performed on the image to obtain color information such as red, green, blue reflection coefficients R1, R2 and R3, and then the turbidity Tur can be estimated by using the following formula:

$$Tur = \frac{e_1 + e_2 R_1 + e_3 R_2 + e_4 R_3}{1 + e_5 R_1 + e_6 R_2 + e_7 R_3},$$

Wherein, e1-e7 respectively represent parameters trained by performing nonlinear regression.

In one embodiment, the image capture device may be placed on the mobile device. In another embodiment, the image capture device may be placed on the removable detection device 130.

Methods, or certain aspects or portions thereof, may take the form of a program code (i.e., executable instructions) embodied in tangible media, such as floppy diskettes, CD-ROMS, hard drives, or any other machine-readable storage medium, wherein, when the program code is loaded into and executed by a machine, such as a computer, the machine thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a machine, such as a computer, the machine becomes an apparatus for practicing the disclosed methods. When implemented on a general-purpose processor, the program code combines with the processor to provide a unique apparatus that operates analogously to application-specific logic circuits.

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the present invention shall be defined and protected by the following claims and their equivalent.

What is claimed is:

1. A tele-care management system for peritoneal dialysis (PD), comprising:
   a container for placing effluent fluid of PD;
   a holder for placing the container; and
   a removable detection device comprising a processor and a communication interface, wherein the removable detection device detects the turbidity and the chrominance of the effluent fluid, and the processor performs a quantitative analysis on the effluent fluid and generates a turbidity prediction value based on the detection result of the removable detection device,
   wherein the communication interface transmits the turbidity prediction value to a mobile device for further processing,
   wherein the processor respectively calculates a first turbidity value which corresponds to a first turbidity for the effluent fluid according to a first algorithm and a second turbidity value which corresponds to a second turbidity for the effluent fluid according to a second algorithm and selects one from the first and second turbidity values based on a predetermined threshold value to generate the turbidity prediction value,
   wherein the removable detection device further comprises an ultrasonic sensor, a light sensor and array-type light-emitting diodes,
   wherein the light sensor and the array-type light-emitting diodes are respectively placed on a corresponding position on the holder, and the processor performs the quantitative analysis on the effluent fluid system using the ultrasonic sensor and detects the turbidity and the chrominance of the effluent fluid using the light sensor and the array-type light-emitting diodes.

2. The tele-care management system of claim 1, wherein the container is made of translucent acrylic material and has a fixed surface area on the surface.

3. The tele-care management system of claim 1, wherein the first algorithm is a Beer's law algorithm and the second algorithm is a scattering or Rayleigh/Mie scattering.

4. The tele-care management system of claim 1, wherein the communication interface is used for transmitting the turbidity prediction value generated to a mobile device application on the mobile device.

5. The tele-care management system of claim 4, wherein the mobile device application further provides a graphical user interface to transmit an analysis request to the removable detection device to obtain and display the turbidity prediction value.

6. The tele-care management system of claim 4, where the mobile device application further stores the turbidity prediction value and uploads the turbidity prediction value to a cloud system.

7. The tele-care management system of claim 6, wherein the mobile device application further captures an image corresponding to the effluent fluid and performs a color calibration and compensation operation on the captured image to analyze the turbidity and chrominance of the effluent fluid.

8. A method for peritoneal dialysis (PD) applied to a tele-care management system for PD, comprising:
receiving an analysis request;
in response to the analysis request, using a removable detection device to perform a quantitative analysis on an effluent fluid of PD and respectively calculate a first turbidity value which corresponds to a first turbidity for the effluent fluid according to a first algorithm and a second turbidity value which corresponds to a second turbidity for the effluent fluid according to a second algorithm;
selecting one from the first and second turbidity values to generate a turbidity prediction value based on a predetermined threshold value; and
transmitting the turbidity prediction value to a mobile device application for display, wherein the removable detection device further comprises an ultrasonic sensor, a light sensor, array-type light-emitting diodes and a processor, wherein the light sensor and the array-type light-emitting diodes are respectively placed on a corresponding position on the holder, and the processor performs the quantitative analysis on the effluent fluid system using the ultrasonic sensor and detects the turbidity and the chrominance of the effluent fluid using the light sensor and the array-type light-emitting diodes.

9. The method of claim 8, wherein the first algorithm is a Beer's law algorithm and the second algorithm is a scattering or Rayleigh/Mie scattering method.

10. The method of claim 8, wherein the mobile device application further provides a graphical user interface to transmit the analysis request to the removable detection device to obtain and display the turbidity prediction value.

11. The method of claim 8, where the mobile device application further stores the turbidity prediction value and uploads the turbidity prediction value to a cloud system.

12. The method of claim 8, wherein the mobile device application further captures an image corresponding to the effluent fluid and performs a color calibration and compensation operation on the captured image to analyze the turbidity and chrominance of the effluent fluid.

* * * * *